United States Patent [19]
Goel

[11] Patent Number: 4,709,040
[45] Date of Patent: Nov. 24, 1987

[54] OXAZOLINE CONTAINING MULTIFUNCTIONAL MONOMER

[75] Inventor: Anil B. Goel, Worthington, Ohio

[73] Assignee: Ashland Oil, Inc., Ashland, Ky.

[21] Appl. No.: 899,198

[22] Filed: Aug. 21, 1986

[51] Int. Cl.$^4$ .................. C07D 263/08; C07D 413/00
[52] U.S. Cl. .................................... 548/237; 526/260; 528/363
[58] Field of Search ............................... 548/237, 215

[56] References Cited

U.S. PATENT DOCUMENTS 4,247,671  1/1981  Reitz et al. ....................... 526/260

Primary Examiner—Harold D. Anderson
Attorney, Agent, or Firm—John F. Jones

[57] ABSTRACT

A thermally polymerizable monomer of formula:

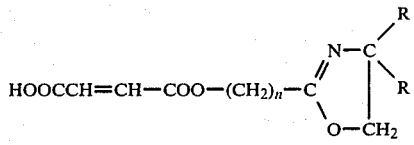

is prepared by reaction of maleic anhydried and a hydroxy 2-oxazoline of formula:

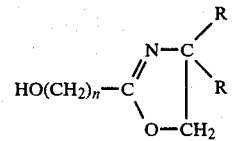

wherein R independently represents hydrogen or a hydrocarbon group having from 1 to 20 carbon atoms.

4 Claims, No Drawings

OXAZOLINE CONTAINING MULTIFUNCTIONAL MONOMER

This invention relates to novel monomers containing both oxazoline and vinyl functional groups in a single molecule and more particularly pertains to such monomers which are obtained by reaction of certain hydroxyl group containing oxazolines and maleic anhydride and to the highly cross linked polymers which result from the thermal polymerization of said monomers.

Mono and bisoxazolines are known to react with various organic reagents leading to various types of polymers [see *Angew Chem. Int. Edn.* 5, 875 (1966) and *Chem. Rev.*, 71, 483 (1971)]. The reaction of isopropyl oxazoline with maleic anhydride is shown to give a linear polymer [*Angew Chem. Int. Ed.*, 9, 460 (1970)]. Hydroxy alkyl oxazolines have been used in the formation of other oxazoline-containing vinyl monomers (U.S. Pat. No. 4,247,671). There is no previous report of monomers prepared from certain hydroxy alkyl oxazolines and maleic anhydride nor of the highly cross linked polymers resulting from thermal polymerization of these monomers.

I have discovered that hydroxy alkyl-2-oxazolines of the formula:

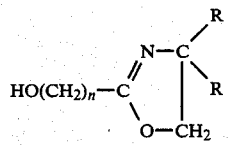

with maleic anhydride produces a multifunctional monomer having the formula:

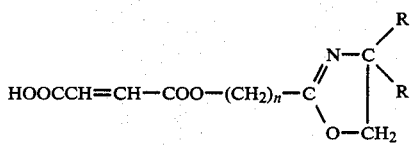

wherein R independently represents hydrogen or a hydrocarbon group having from 1 to 20 carbon atoms and n is a number of from 1 to 20. This monomer when heated to a temperature in the range of from about 25° to 200° C. and preferably from about 100° C. to 300° C., forms a highly crosslinked polymer which is insoluble and infusible.

The crosslinked polymers of this invention have been found to be insoluble in most of the common organic solvents including toluene, acetone, tetrahydrofuran, dimethyl formamide, and the like. These polymers have been found to be tough and somewhat brittle at lower temperatures but become somewhat rubbery at temperatures above about 200° C. These polymers are useful in blends with other polymers for improving performance in adhesives, coatings, and the like applications.

This invention is further illustrated in the following representative examples.

EXAMPLE 1

This example illustrates the preparation of 5-hydroxypentyl-2-oxazoline. To 61 g of ethanol amine placed in a 500 ml round bottomed flask was added dropwise with stirring 114 g of epsilon-caprolactone and the addition was done over a period of about two hours. The resulting reaction product (amide diol) was placed in a dropping funnel which was mounted on the top of a column reactor containing activated alumina in the column. This reactor was connected to a three neck flask which was connected to a vacuum pump. The reactor was heated at 300° C. and whole assembly was evacuated to 0.1 mm of Hg. The amide-diol was added dropwise to the alumina in the column from the heated (100° C.) dropping funnel. As the liquid amide-diol was contacted with the hot alumina it underwent cyclization-dehydration to give 5-hydroxy pentyl-2-oxazoline, the vapors of which were condensed in the flask which was kept at 0° C. A yield of 85% of product was obtained. The product was redistilled under reduced pressure at 90° C. and at 0.1 mm pressure as a light pale colored liquid. Other hydroxy alkyl-2-oxazolines were prepared in a similar manner.

EXAMPLE 2

This example describes the preparation of 2-(5-hydroxypentyl)-1(4,4'-dimethyl)-2-oxazoline. Epsilon caprolactone (115 g) was added to 130 g of HOCH$_2$C(CH$_3$)$_2$NH$_2$ (methyl propanol amine) with stirring. The reaction mixture was then heated at 150°–240° C. and the water produced in the reaction was distilled through a 3' long fractionating column during the five hour reaction period. Excess methyl propanol amine was distilled out (total reaction time of ten hours). The material in the reactor was then subjected to vacuum distillation at 110°–115° C. and 0.4–0.5 mm (150 g) was collected and GLC analysis shows it to be 99% pure 2-(5-hydroxypentyl)-(4,4'-dimethyl)-2-oxazoline. Other oxazolines using other lactones were prepared in a similar manner.

EXAMPLE 3

This example illustrates the preparation of a multifunctional monomer of this invention. A mixture of 18.5 g of 2-(5-hydroxypentyl)-(4,4'-dimethyl)-2-oxazoline and 9.7 g of maleic anhydride was allowed to react at room temperature for a short time. A viscous liquid resulted upon mixing which stayed in the viscous liquid form at room temperature for over a one month period. The product was identified as having the structure

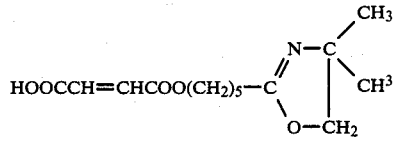

Other monomers having the general formula

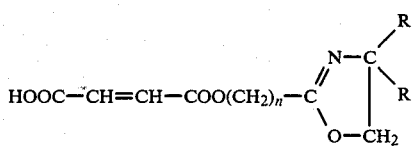

wherein R has the foregoing designation were prepared in a similar fashion.

EXAMPLE 4

This example illustrates the formation of a highly crosslinked polymer from the monomers of this invention. The procedure of Example 3 was repeated using 18.8 g of the hydroxy alkyl oxazoline and 10.5 g of maleic anhydride. The resulting viscous liquid was dissolved in 50 ml of acetone to give a clear solution. A cloth made of glass fibers which was about 2½ inches wide and 50 inches long was dipped into the solution and was kept at room temperature for about 30 minutes during which time the acetone was allowed to evaporate. Ten pieces of approximately 4½ inches in length were then cut from the treated cloth and placed on top of each other and between two aluminum foils. This sandwich was placed in a steel mold and allowed to cure at between 100° and 120° C. for three hours followed by post curing at 150°–180° C. for three hours. The resulting glass fiber reinforced composite sheet (having about 60% by weight of glass) showed a notched izod impact strength (ASTM D256) of 16.7 foot pounds/inch of notch, and an ASTM D790 flexural modulus of 1,115,780 psi.

I claim:

1. The process for preparing a multifunctional monomer of the formula:

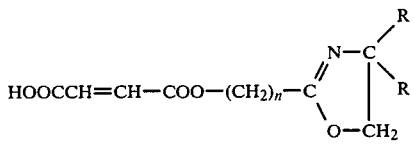

by reacting maleic anhydride with a hydroxy alkyl 2-oxazoline of the formula:

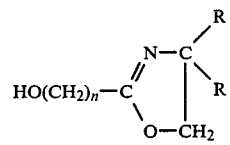

wherein R independently represents hydrogen or a hydrocarbon group having from 1 to 20 carbon atoms and n is a number of from 1 to 20.

2. The process of claim 1 wherein n is 5 and R represents hydrogen.

3. The process of claim 1 wherein n is 5 and R represents methyl.

4. The multifunctional monomer produced by the process of claim 1.

* * * * *